(12) United States Patent
Baxter et al.

(10) Patent No.: US 9,149,573 B2
(45) Date of Patent: Oct. 6, 2015

(54) BLUNT CANNULA FOR ACCESSING A SLIT SEPTUM

(75) Inventors: Charles S. Baxter, Worthington, OH (US); Dale Marvin Gallogly, Mount Vernon, OH (US); Theodore J. Mosler, Raleigh, NC (US); Charles R. Patzer, Columbus, OH (US)

(73) Assignee: Smiths Medical ASD, Inc., Rockland, MA (US)

(*) Notice: Subject to any disclaimer, the term of this patent is extended or adjusted under 35 U.S.C. 154(b) by 1529 days.

(21) Appl. No.: 11/687,533

(22) Filed: Mar. 16, 2007

(65) Prior Publication Data

US 2008/0228149 A1    Sep. 18, 2008

(51) Int. Cl.
| | | |
|---|---|---|
| *A61M 3/00* | (2006.01) | |
| *A61M 3/02* | (2006.01) | |
| *A61M 39/04* | (2006.01) | |
| *A61M 39/26* | (2006.01) | |

(52) U.S. Cl.
CPC . *A61M 3/00* (2013.01); *A61M 3/02* (2013.01); *A61M 3/0283* (2013.01); *A61M 39/045* (2013.01); *A61M 39/26* (2013.01)

(58) Field of Classification Search
CPC ........ A61M 3/0283; A61M 3/02; A61M 3/00
USPC ............ 604/164.11, 244, 273, 274, 525, 264, 604/272, 533
See application file for complete search history.

(56) References Cited

U.S. PATENT DOCUMENTS

| | | | |
|---|---|---|---|
| 2,458,063 A | | 3/1947 | Dulberg |
| D165,691 S | | 1/1952 | Macomic |
| 2,716,983 A | * | 9/1955 | Ryan et al. ............. 604/274 |
| 2,989,053 A | | 1/1956 | Hamilton |
| 2,954,768 A | * | 10/1960 | Hamilton ............. 604/274 |
| 3,093,134 A | * | 6/1963 | Roehr ............. 604/272 |
| 3,352,531 A | | 11/1967 | Kilmarx |
| 3,565,074 A | * | 2/1971 | Foti ............. 604/164.11 |
| 3,726,282 A | | 4/1973 | Patel |
| 4,058,121 A | * | 11/1977 | Choksi et al. ............. 604/411 |
| 4,106,491 A | | 8/1978 | Guerra |
| D270,568 S | | 9/1983 | Armstrong |

(Continued)

FOREIGN PATENT DOCUMENTS

| | | |
|---|---|---|
| EP | 0050459 B1 | 2/1985 |
| EP | 0309771 B1 | 4/1992 |

(Continued)

OTHER PUBLICATIONS

Contiguous. (2007). In the American Heritage Dictionary of the English Language. Retrieved from http://www.credoreference.com/entry/hmdictenglang/contiguous.*

(Continued)

*Primary Examiner* — Aarti B Berdichevsky
*Assistant Examiner* — Matthew A Engel
(74) *Attorney, Agent, or Firm* — Wood, Herron & Evans, LLP (57) ABSTRACT

A blunt cannula includes a distal portion and a proximal portion. The distal portion has a non-uniform taper defined by a plurality, such as four, differently tapered segments. The proximal portion may additionally or alternatively have a non-circular, such as oval, cross-section. At least the major diameter (D.sub.MAJ) of the proximal portion my taper toward the distal portion.

43 Claims, 8 Drawing Sheets

(56) References Cited

U.S. PATENT DOCUMENTS

| | | | |
|---|---|---|---|
| 4,411,657 A * | 10/1983 | Galindo | 604/274 |
| 4,512,766 A | 4/1985 | Vailancourt | |
| 4,513,754 A * | 4/1985 | Lee | 600/566 |
| D282,284 S | 1/1986 | McCord et al. | |
| 4,578,063 A | 3/1986 | Inman et al. | |
| 4,610,374 A * | 9/1986 | Buehler | 222/83 |
| 4,643,712 A * | 2/1987 | Kulik et al. | 604/6.16 |
| 4,699,612 A * | 10/1987 | Hamacher | 604/506 |
| 4,710,180 A | 12/1987 | Johnson | |
| 4,758,225 A | 7/1988 | Cox et al. | |
| 4,795,446 A | 1/1989 | Fecht | |
| 4,834,716 A | 5/1989 | Ogle, II | |
| 4,850,354 A * | 7/1989 | McGurk-Burleson et al. | 606/170 |
| 4,904,238 A | 2/1990 | Williams | |
| 4,908,018 A | 3/1990 | Thomsen | |
| 4,959,049 A * | 9/1990 | Smirmaul | 604/22 |
| 4,983,160 A | 1/1991 | Steppe et al. | |
| 4,985,027 A * | 1/1991 | Dressel | 606/15 |
| D314,622 S | 2/1991 | Andersson et al. | |
| D321,252 S | 10/1991 | Jepson et al. | |
| 5,071,413 A * | 12/1991 | Utterberg | 604/533 |
| 5,098,407 A | 3/1992 | Okamura | |
| 5,100,394 A * | 3/1992 | Dudar et al. | 604/537 |
| 5,112,318 A | 5/1992 | Novacek et al. | |
| 5,114,400 A | 5/1992 | Lynn | |
| 5,135,489 A * | 8/1992 | Jepson et al. | 604/48 |
| 5,149,327 A | 9/1992 | Oshiyama | |
| 5,158,554 A | 10/1992 | Jepson et al. | |
| 5,183,469 A | 2/1993 | Capaccio | |
| 5,188,593 A | 2/1993 | Martin | |
| 5,199,948 A | 4/1993 | McPhee | |
| 5,201,717 A | 4/1993 | Wyatt et al. | |
| 5,221,271 A | 6/1993 | Nicholson et al. | |
| 5,248,056 A | 9/1993 | Shaw | |
| 5,254,106 A * | 10/1993 | Feaster | 604/272 |
| 5,295,980 A * | 3/1994 | Ersek | 604/272 |
| 5,312,346 A | 5/1994 | Han | |
| 5,322,516 A * | 6/1994 | Brugger | 604/192 |
| 5,334,188 A | 8/1994 | Inoue et al. | |
| 5,356,396 A | 10/1994 | Wyatt et al. | |
| 5,389,086 A * | 2/1995 | Attermeier et al. | 604/242 |
| D357,735 S | 4/1995 | McPhee | |
| 5,417,673 A | 5/1995 | Gordon | |
| D362,718 S | 9/1995 | Deily et al. | |
| 5,447,495 A | 9/1995 | Lynn et al. | |
| 5,453,089 A | 9/1995 | Brugger | |
| 5,464,123 A | 11/1995 | Scarrow | |
| 5,466,219 A | 11/1995 | Lynn et al. | |
| 5,474,546 A | 12/1995 | Ambrisco et al. | |
| 5,478,329 A * | 12/1995 | Ternamian | 604/274 |
| 5,501,676 A | 3/1996 | Niedospial et al. | |
| 5,531,694 A | 7/1996 | Clemens et al. | |
| 5,569,222 A * | 10/1996 | Haselhorst et al. | 604/533 |
| 5,599,321 A | 2/1997 | Conway et al. | |
| 5,603,706 A | 2/1997 | Wyatt et al. | |
| 5,632,735 A | 5/1997 | Wyatt et al. | |
| 5,639,810 A | 6/1997 | Smith, III et al. | |
| 5,643,226 A * | 7/1997 | Cosgrove et al. | 604/264 |
| 5,658,260 A * | 8/1997 | Desecki et al. | 604/239 |
| D393,722 S | 4/1998 | Fangrow, Jr. et al. | |
| 5,772,255 A | 6/1998 | Osborne et al. | |
| RE35,841 E | 7/1998 | Frank et al. | |
| 5,776,125 A | 7/1998 | Dudar et al. | |
| 5,810,792 A | 9/1998 | Fangrow et al. | |
| 5,833,674 A | 11/1998 | Turnbull et al. | |
| 5,848,996 A * | 12/1998 | Eldor | 604/272 |
| 5,947,954 A | 9/1999 | Bonaldo | |
| D416,086 S | 11/1999 | Parris et al. | |
| 5,976,115 A | 11/1999 | Parris et al. | |
| 6,029,946 A | 2/2000 | Doyle | |
| 6,050,978 A | 4/2000 | Orr et al. | |
| D424,192 S | 5/2000 | Shulze | |
| 6,090,066 A | 7/2000 | Schnell | |
| 6,146,362 A * | 11/2000 | Turnbull et al. | 604/256 |
| 6,171,287 B1 | 1/2001 | Lynn et al. | |
| 6,193,697 B1 | 2/2001 | Jepson et al. | |
| 6,217,568 B1 | 4/2001 | Jepson et al. | |
| 6,387,086 B2 | 5/2002 | Mathias et al. | |
| 6,391,014 B1 | 5/2002 | Silverman | |
| 6,447,498 B1 | 9/2002 | Jepson et al. | |
| 6,481,679 B1 | 11/2002 | Bennett et al. | |
| 6,500,157 B2 * | 12/2002 | Luther | 604/264 |
| 6,551,289 B1 * | 4/2003 | Higuchi et al. | 604/272 |
| 6,569,125 B2 | 5/2003 | Jepson et al. | |
| 6,610,005 B1 | 8/2003 | Tao | |
| 6,706,023 B1 * | 3/2004 | Huttner et al. | 604/264 |
| 6,838,050 B1 | 1/2005 | Green et al. | |
| 7,056,308 B2 * | 6/2006 | Utterberg | 604/256 |
| 7,081,109 B2 | 7/2006 | Tighe et al. | |
| 7,140,592 B2 | 11/2006 | Phillips | |
| 7,144,396 B2 * | 12/2006 | Shluzas | 606/266 |
| D540,469 S | 4/2007 | Grabinsky | |
| 7,217,246 B1 | 5/2007 | Stone | |
| 7,247,153 B2 * | 7/2007 | Guala | 604/414 |
| D570,475 S | 6/2008 | Mosler | |
| D570,477 S | 6/2008 | Gallogly | |
| D571,006 S | 6/2008 | Baxter | |
| D571,464 S | 6/2008 | Baxter | |
| D572,820 S | 7/2008 | Gallogly | |
| D574,491 S | 8/2008 | Baxter | |
| D577,438 S | 9/2008 | Gallogly | |
| D577,820 S | 9/2008 | Mosler | |
| D577,821 S | 9/2008 | Mosler | |
| D577,822 S | 9/2008 | Gallogly | |
| D578,214 S | 10/2008 | Mosler | |
| D581,526 S | 11/2008 | Mosler et al. | |
| D582,033 S | 12/2008 | Baxter | |
| D582,550 S * | 12/2008 | Baxter et al. | D24/130 |
| 7,615,041 B2 * | 11/2009 | Sullivan et al. | 604/411 |
| 7,666,172 B2 * | 2/2010 | Atil | 604/272 |
| 7,708,714 B2 * | 5/2010 | Connell et al. | 604/30 |
| 7,713,249 B2 * | 5/2010 | Lopez | 604/249 |
| 2002/0087144 A1 | 7/2002 | Zinger et al. | |
| 2002/0143297 A1 | 10/2002 | Francavilla et al. | |
| 2002/0143298 A1 | 10/2002 | Marsden | |
| 2003/0106917 A1 | 6/2003 | Shetler et al. | |
| 2003/0120221 A1 | 6/2003 | Vaillancourt | |
| 2004/0002684 A1 * | 1/2004 | Lopez | 604/240 |
| 2004/0006319 A1 | 1/2004 | Lina et al. | |
| 2004/0049892 A1 | 3/2004 | Messina | |
| 2004/0220542 A1 | 11/2004 | Cise et al. | |
| 2004/0227120 A1 | 11/2004 | Raybuck | |
| 2004/0254541 A1 | 12/2004 | Wong et al. | |
| 2005/0090805 A1 | 4/2005 | Shaw et al. | |
| 2005/0149060 A1 | 7/2005 | Thorstenson et al. | |
| 2005/0159730 A1 * | 7/2005 | Kathrani et al. | 604/541 |
| 2005/0166924 A1 | 8/2005 | Thomas et al. | |
| 2005/0245847 A1 * | 11/2005 | Schaeffer | 600/585 |
| 2005/0261637 A1 | 11/2005 | Miller | |
| 2006/0284036 A1 | 12/2006 | Aube | |
| 2007/0197856 A1 | 8/2007 | Gellman et al. | |

FOREIGN PATENT DOCUMENTS

| | | |
|---|---|---|
| EP | 1391219 | 2/2004 |
| EP | 1391220 | 2/2004 |
| EP | 1726867 A | 11/2006 |
| GB | 2040379 A | 8/1980 |
| WO | 9011103 | 4/1990 |
| WO | 9119462 A1 | 12/1991 |
| WO | 9422524 | 10/1994 |
| WO | 9641649 | 12/1996 |
| WO | 9850106 | 11/1998 |
| WO | 2005021069 A | 3/2005 |

OTHER PUBLICATIONS

Partial European Search Report for EP 07253303.7 dated Mar. 4, 2008 (6 pages).

International Search Report for PCT/US2007/07086 dated Mar. 4, 2008 (7 pages).

Written Opinion for PCT/US2007/07086 dated Mar. 4, 2008 (12 pages).

(56) References Cited

OTHER PUBLICATIONS

Photograph of SECURE sample site and shielded needle.
Photograph of VAMP sample site and blunt cannula/adaptor.
Photograph of SAFESET sample site and blunt cannula/adaptor.
Partial International Search Report for PCT/US2007/070086 mailed on Dec. 7, 2007 (3 pages).
Official Action received in divisional U.S. Appl. No. 12/403,582 mailed Jul. 1, 2009 (9 pages).
Official Action received in divisional U.S. Appl. No. 12/403,588 mailed Jun. 22, 2009 (8 pages).
Official Action received in divisional U.S. Appl. No. 12/403,593 mailed Jun. 22, 2009 (9 pages).
European Search Report and Preliminary Written Opinion received in related divisional European Application No. EP 09 00 4792 Jul. 9, 2009 (5 pages).
European Search Report and Preliminary Written Opinion received in related divisional European Application No. EP 09 00 4793 dated May 18, 2009 (7 pages).
European Search Report and Preliminary Written Opinion received in related divisional European Application No. EP 09 004852 dated Jul. 9, 2009 (4 pages).
Official Action in related U.S. Appl. No. 12/403,582 mailed Nov. 16, 2009 (10 pages).
Official Action in related U.S. Appl. No. 12/403,588 mailed Dec. 2, 2009 (10 pages).
Official Action in related U.S. Appl. No. 12/403,593 mailed Dec. 2, 2009 (9 pages).
Official Action in related U.S. Appl. No. 12/406,588 mailed Feb. 12, 2010 (9 pages).
Official Action in related U.S. Appl. No. 12/403,588 mailed Jun. 29, 2010 (10 pages).
European Patent Office, Office Communication Pursuant to Article 94(3) EPC in EP Application No. 07 253 303.7—1504, May 15, 2015.

* cited by examiner

BLUNT CANNULA FOR ACCESSING A SLIT SEPTUM

FIELD OF THE INVENTION

The present invention relates to blunt cannulas used to access a slit septum and adaptors having blunt cannulas to access slit septums of medical sites, such as sample sites or injection sites. In another aspect, the present invention relates to a sample site.

DESCRIPTION OF PRIOR ART

Sample sites and injections sites typically comprise a plastic housing with one or more ports for fluid ingress or egress relative to the interior cavity of the housing. The housing also typically has a cylindrical portion defining a large aperture adjacent the cavity but which is closed off by a solid septum. A sharp needle may be inserted through the material of the septum to bring the distal opening of the needle at the sharp tip into communication with fluid within the housing to facilitate fluid flow through the lumen of the needle. To reduce needle-stick risks, the needle is contained within a shroud that is generally sized and shaped to prevent fingers from touching the needle tip. The shroud fits over the cylindrical portion of the housing as the needle extends into and through the septum into the cavity. In some arrangements, the shroud may also include slots positioned and sized to fit over the port(s) of the housing, and further may be shaped, such as to define a J-shape, so as to be rotatable relative to the port(s) to lock the shroud to the site.

In an effort to reduce or eliminate needles, the solid septum is replaced with a slit septum through which a blunt cannula is to be inserted. Typically, the blunt cannula may form part of an adaptor having luer mating structure to connect with the luer structure of a standard medical device, such as a syringe by way of example, in order to fluidicly couple into the site cavity via the central lumen of the blunt cannula. The blunt cannula typically has an upper or proximal circular cross-section cylindrical portion, and a lower or distal portion that tapers to a tip, with the tip defining or including a distal opening for fluid flow relative to the central lumen of the blunt cannula. It has been proposed to control the taper of the distal portion so that it is gradual and uniform between the proximal portion and the tip, which uniform taper is said to reduce insertion forces necessary to insert the cannula through the slit. Also, the proximal portion is intended to be a cylinder without any significant taper, other than perhaps a nominal taper due to draft in the molding process, to reduce the tendency for kick back of the cannula (i.e., the septum material and cannula surface interacting in a manner which would urge the cannula back out of the slit) when the cannula is inserted far enough into the slit to reach the proximal portion of the cannula as is typically desired.

There are various drawbacks with these blunt cannulas. By way of example, the slit may not seal against the proximal portion of the cannula extending therein, thus creating an area for possible fluid leakage. Further, some of the tip ends of the blunt cannula have been found to be quite sharp. While that "sharp" end allows the cannula to make initial entry into the slit, a shroud is still necessary therewith to prevent finger-touching of the tip as was done with the sharp needles these blunt cannula were intended to replace. Alternatively, the tip end or surface of the cannula may be flat and so is desirably blunt rather than sharp. But the flat end can impede initial entry of the cannula into the slit.

SUMMARY OF THE INVENTION

The present invention provides an improved blunt cannula design with a uniquely shaped distal portion so as not to require a tip end that is either essentially sharp or flat while advantageously reducing insertion resistance. In accordance with the principles of the present invention, the distal portion of the blunt cannula presents a rounded tip end or surface, which may be solid, and a plurality of tapered segments having different tapers extending between the proximal portion and the tip end. The differently-tapered segments present a non-uniformly tapering distal portion which is believed to provide the advantage of reduced insertion forces, but without the disadvantage of a tip end that is so sharp as to have need for a protective shroud nor so flat as to impede entry into the septum slit.

The distal portion advantageously includes at least a conically tapered segment and a generally arcuately tapered segment. Further advantageously, there are four differently-tapered segments (by type and/or size). The four segments may alternate between conical and arcuate tapers. A first tapered segment adjacent the proximal portion may extend with a conical taper, followed by a second tapered segment having a generally arcuate taper with a radius of curvature. A third tapered segment may extend with a conical taper, which may advantageously be greater than the conical taper of the first tapered segment, and a fourth tapered segment may lead into the solid, rounded tip and may have a generally arcuate taper with a radius of curvature less than that of the second segment.

In accordance with a further aspect of the present invention, the central lumen of the blunt cannula extends distally through the proximal portion and only partially into the distal portion. Advantageously, the central lumen does not extend into the distal portion so far as to reach the solid, rounded tip end and further advantageously not so far as to reach even the lowermost tapered segment. To that end, some aspect of the tapered segment adjacent the tip (or that entire segment and possibly some aspect of the next, proximally adjacent segment) is solid. The fluid opening(s) of the distal portion coupling to the central lumen pass through one or more of the tapered segments, excluding the solid aspect(s) of the tapered segment. As a result, the fluid path to and from the central lumen via the fluid opening(s) advantageously will not extend into or through the tip so as not to interfere with the solid, rounded tip. A groove(s) may extend distally from the fluid opening(s) along some or all of the solid aspect(s) of the tapered segments toward, but not necessarily all the way, to the tip end. The fluid opening(s) may also extend through aspects of the proximal portion of the blunt cannula, particularly the aspect thereof closely adjacent to the distal portion of the blunt cannula.

The present invention may also or alternatively provide an improved blunt cannula design with a uniquely shaped proximal portion by which to enhance the seal between the septum slit and the blunt cannula during use. To that end, and in accordance with the principles of the present invention, the proximal portion of the blunt cannula may have a non-circular cross-section instead of a circular cross-section. Advantageously, the proximal portion is not a cylinder. In that regard, the cross-section of the proximal portion, at least along a substantial length thereof, is generally oval and tapers distally such that the major diameter of the oval cross-section decreases therealong to merge into the first tapered portion of the distal portion. It is believed that the shape created upon opening of the slit is not circular. The shaping of the proximal portion to have a generally oval cross-section is thus believed to afford a more complete seal between the surfaces of the slit and the blunt cannula during use. Yet, while the tapering of the major diameter of the proximal portion, along with the non-uniform taper of the distal portion, results in a blunt cannula that has a significant taper along substantially its entire length, it is believed that kickback is not problematic.

The blunt cannula of the present invention may form part of an adaptor to be used with a medical site, for example. In that regard, the medical site may be a sample site with oppositely disposed fluid ports extending from a central housing containing the septum to define a T-shape to the medical site. With such a T-shaped construction, fluid flows between the ports and across the septum. The central housing may be cylindrical, and support the septum at the top thereof adjacent the flow path. The adaptor has a plate with luer mating structure, such as a male luer lock, associated with one surface thereof and the blunt cannula extending from the opposite surface thereof with the central lumen of the cannula in fluid communication with the luer mating structure. Depending from opposite edges of the plate to either side of the blunt cannula is a pair of oppositely disposed, generally flat guide walls. The guide walls may have lateral edges extending into the area below the intermediate edges of the plate. Advantageously, the cannula may be spaced equidistant from the two guide walls. Further advantageously, the guide walls are spaced apart a distance approximating the diameter of the central housing such that the guide walls and housing cooperate to align the tip of the cannula with the slit of the septum for proper insertion therewith. One or more of the outboard or lateral edges of the guide walls may be provided with a rib aimed toward the blunt cannula and which further cooperates to align the blunt cannula to the slit.

The flat guide walls may be spaced apart enough to provide a distal mouth that is large enough not to preclude finger touching. The lateral edges of the flat guide walls may extend into the area below the intermediate edges of the plate sufficient to define a gap that conforms to the width of the port(s) so as to reduce the likelihood of rotation of the adaptor relative to the housing with the cannula inserted into the septum. While the guide walls could be shaped and positioned differently to provide a shroud and/or the ability to lock same to the site, it is not believed necessary to do so with the blunt cannula of the present invention and/or the adaptor containing same.

The outboard walls of the housing between the ports of the medical site could be generally flat rather than arcuate, such as by thickening the plastic thereat. The generally flat sides of the housing would cooperate with the generally flat guide walls to further enhance alignment and/or resist rotation. Advantageously, one or more of the lateral edges of the flat side walls of the housing define a groove edge to receive the rib(s) of the guide walls therealong to still further enhance alignment and/or resist rotation.

Where the proximal portion of the blunt cannula has a generally oval-cross-section, the cannula is advantageously inserted into the slit with the major diameter of the generally oval cross-section proximal portion aligned with the slit. To that end, the septum is generally affixed to the site housing aperture with the slit in a fixed orientation relative to the flow path between the ports. The blunt cannula and guide walls of the adaptor are fixed in relationship such that the major diameter of the proximal portion of the blunt cannula extends at an orientation thereto corresponding to the orientation of the slit of the septum relative to the fluid ports. Advantageously for the present invention, the slit orientation may be transverse to that flow path, in which case the blunt cannula is oriented in the adaptor with the major diameter transverse to the guide walls (i.e., with the minor diameter thereof parallel to the guide walls). The gap(s) between the lateral edges of the guide walls and/or the interaction of the rib(s) of the adaptor and the groove edge(s) of the site housing resist rotation of the blunt cannula aligned into the slit.

By virtue of the foregoing, there is thus provided an improved blunt cannula design with a uniquely shaped distal portion so as not to require a tip that is either essentially sharp or flat while advantageously reducing insertion resistance. There is thus also provided an improved blunt cannula design with an uniquely shaped proximal portion by which to enhance the seal between the septum slit and the blunt cannula during use. There is further also provided an adaptor with the improved blunt cannula design(s) for use in accessing the slit septum of medical sites. There is still further provided a medical site configured to advantageously mate with the adaptor. These and other objects and advantages of the present invention shall be made apparent from the accompanying drawings and the description thereof.

BRIEF DESCRIPTION OF THE DRAWINGS

The accompanying drawings, which are incorporated in and constitute a part of this specification, illustrate embodiments of the invention and, together with the general description of the invention given above and the detailed description of the embodiments given below, serve to explain the principles of the present invention.

DETAILED DESCRIPTION OF THE DRAWINGS

With reference to FIGS. 1 through 4, there is shown an embodiment of a blunt cannula 10 in accordance with the principles of the present invention. Cannula 10 includes a proximal or upper portion 12 and a distal or lower portion 14, the latter terminating in a tip segment 16 including a rounded tip end or surface 18. In accordance with one aspect of the present invention, the distal portion 14 is tapered non-uniformly. To that end, distal portion 14 includes a plurality of tapered segments 22, 24, 26, 28 each progressively closer to tip end 18 and each having a different taper as will be described hereinafter. First tapered segment 22 is adjacent proximal portion 12, second tapered segment 24 is adjacent first tapered segment 22, third tapered segment 26 is adjacent second tapered segment, and fourth tapered segment 28 is adjacent third tapered segment and tip segment 16 so as to be closer to tip end 18 than tapered segments 22, 24, or 26.

Advantageously, the tapered segments 22, 24, 26, 28 alternate between conical and arcuate tapers. To that end, first and third tapered segments 22, 26 have conical tapers and second and fourth tapered segments 24, 28 have arcuate tapers. The taper of the third tapered segment 26 is advantageously larger than that of the first tapered segment 22. By way of example, the taper of the first tapered segment 22 may be about 1° while that of the third tapered segment may be about 5°. The arcuate tapers of the second and fourth tapered segments 24 and 28 may also differ, with the radius of curvature of the latter smaller than that of the former. To that end, the radius of curvature of the second tapered segment 24 may be about ¼ inch while that of the fourth tapered segment may be slightly greater than 1/16 inch. The tip segment 16 may have a radius of about 1/36 inch to define rounded end 18.

In accordance with a further aspect of the present invention, the proximal portion 12 advantageously has a non-circular cross-section such as an oval cross section as seen particularly in FIGS. 3, 4, 5A, and 5B. The proximal portion 12 may taper from its upper end 30 and opening 31 thereat toward the distal portion 14 such that the major diameter ($D_{MAJ}$) thereof decreases to facilitate merger of the proximal and distal portions 12, 14. The minor diameter ($D_{MIN}$) of the proximal portion 12 may also taper along its length if desired.

Figure 1:
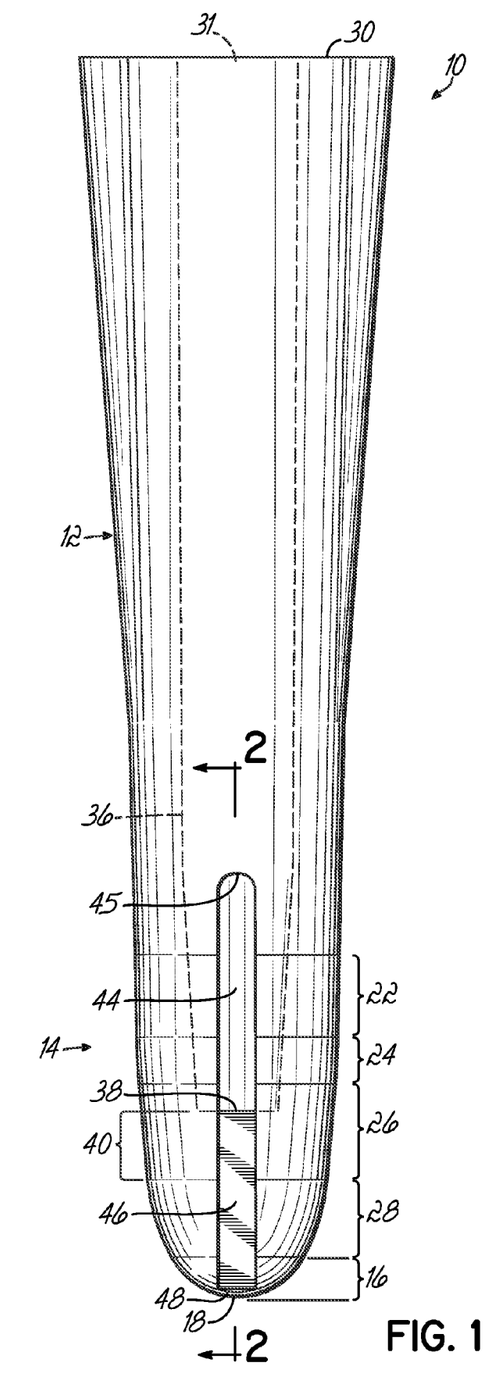
FIG. 1 is a front elevation view of a blunt cannula in accordance with the principles of the present invention.
Figure 2:
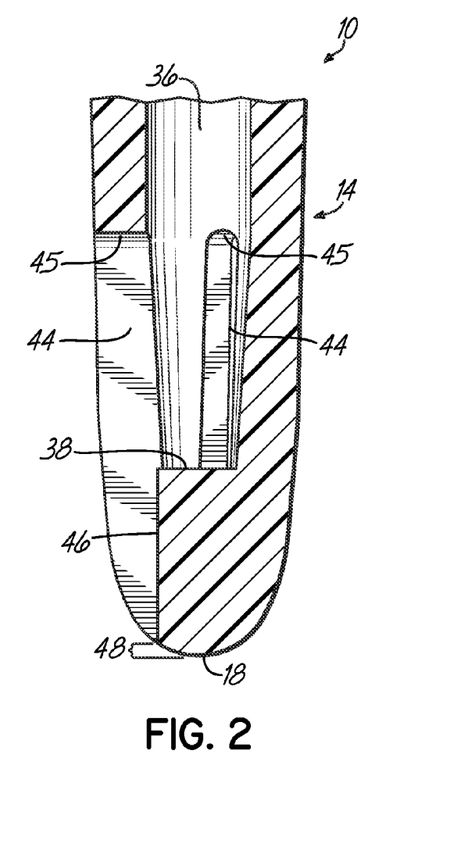
FIG. 2 is a cross-sectional view of the blunt cannula of FIG. 1 taken along line 2-2.
Figure 3:
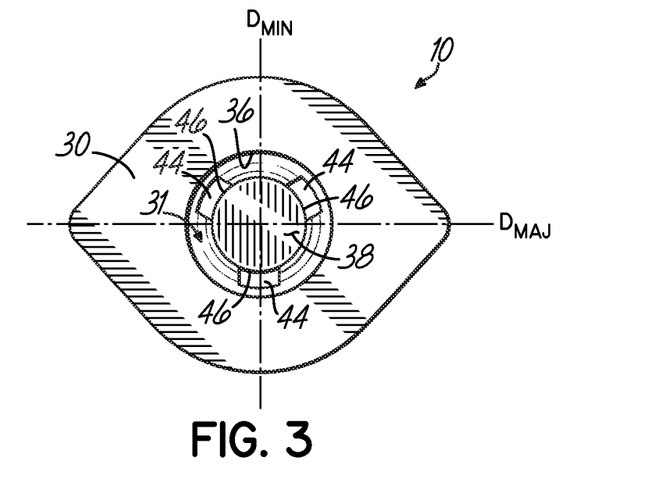
FIG. 3 is a top or proximal plan view of the blunt cannula taken of FIG. 1.
Figure 4:
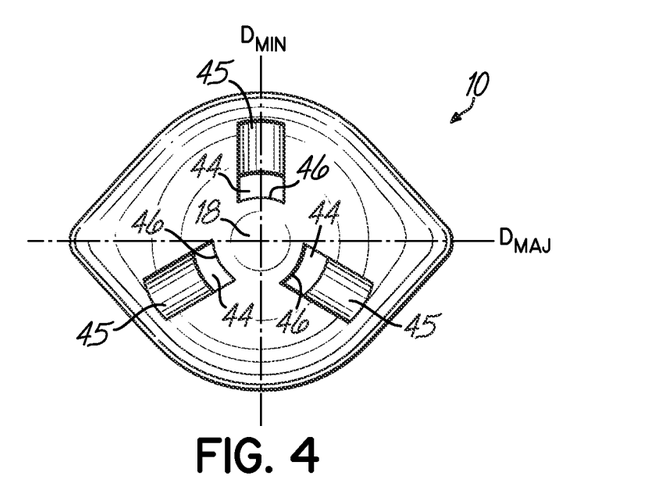
FIG. 4 is a bottom or distal plan elevation view of the blunt cannula of FIG. 1.

A fluid lumen 36 extends centrally from the upper end opening 31 of cannula 10 through proximal portion 12 and partially into distal portion 14, but terminates as at 38 spaced away from tip end 18. Advantageously, lumen 36 extends through the first and second tapered segments 22, 24 but only partially into third tapered segment 26, such that the rest 40 of tapered segment 26, and all of fourth tapered segment 28 and tip segment 16 are solid. Fluid communication is established with central lumen 36 via one or more fluid openings 44 extending through an aspect of proximal portion 12 as at 45 and the portions of first, second and third tapered segments 22, 24, 26 coextensive with lumen 36, excluding the solid portion 40 of tapered segment 26 and all of solid tapered segment 28 and solid tip segment 16, such that the fluid path to and from the central lumen 36 via the fluid opening 44 does not extend into or through tip end 18. As shown in FIG. 4, there may be three fluid openings 44 circumferentially and equidistantly spaced about cannula 10. Fluid openings 44 each communicate with a respective groove 46 extending from lumen 36 at 38, distally along solid aspect 40 of tapered segment 26 and solid segment 28 formed in the solid aspects thereof. Each groove 46 may also extend partially along solid tip segment 16, but the grooves 46 advantageously do not extend so far into the material of cannula 10 as to reach all the way to tip end 18 (as exemplified by the area 48 in FIG. 2).

Figure 5A:
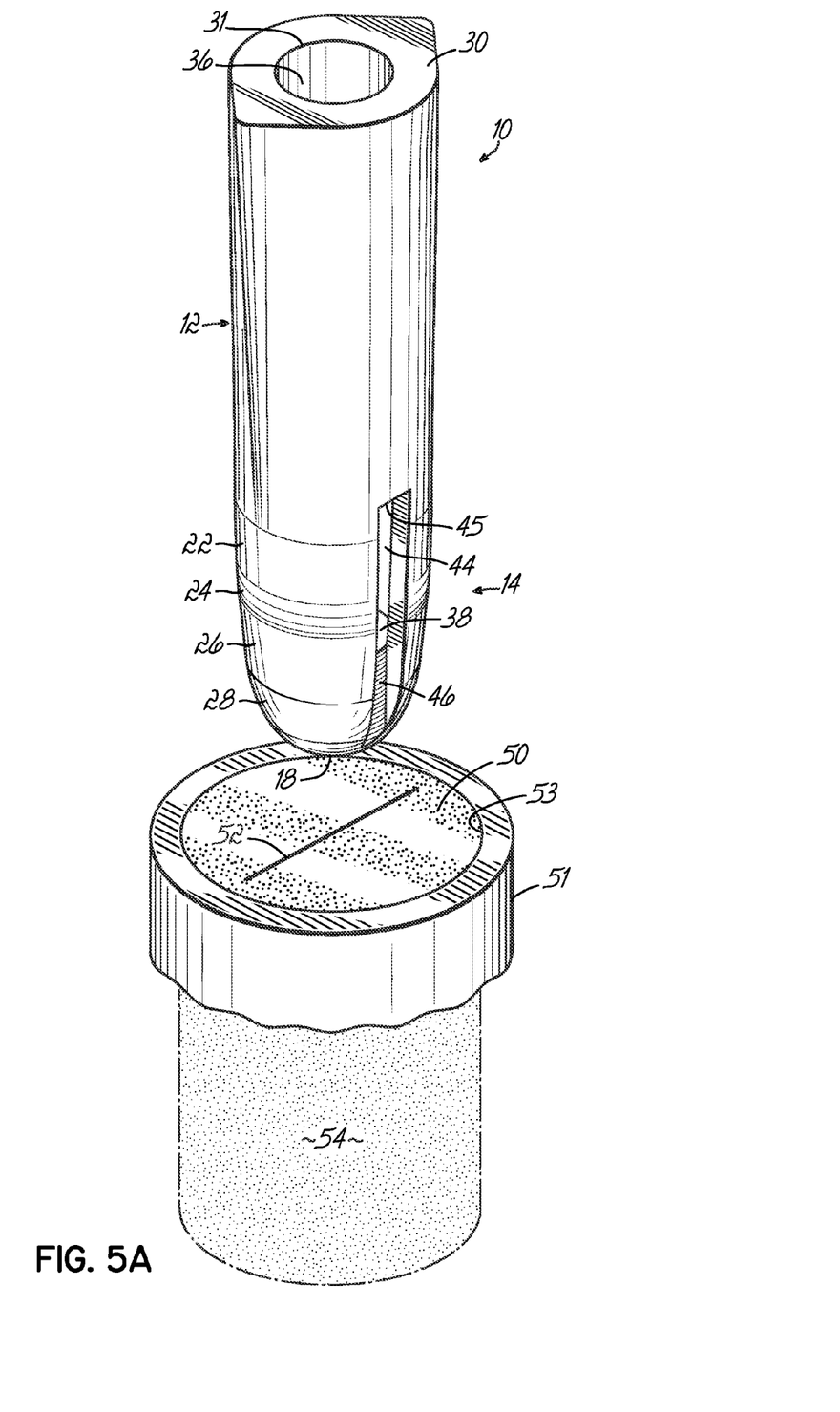
FIGS. 5A and 5B are a partial perspective views of the blunt cannula of FIG. 1 and a slit septum showing the blunt cannula out of and within the slit, respectively.
Figure 5B:
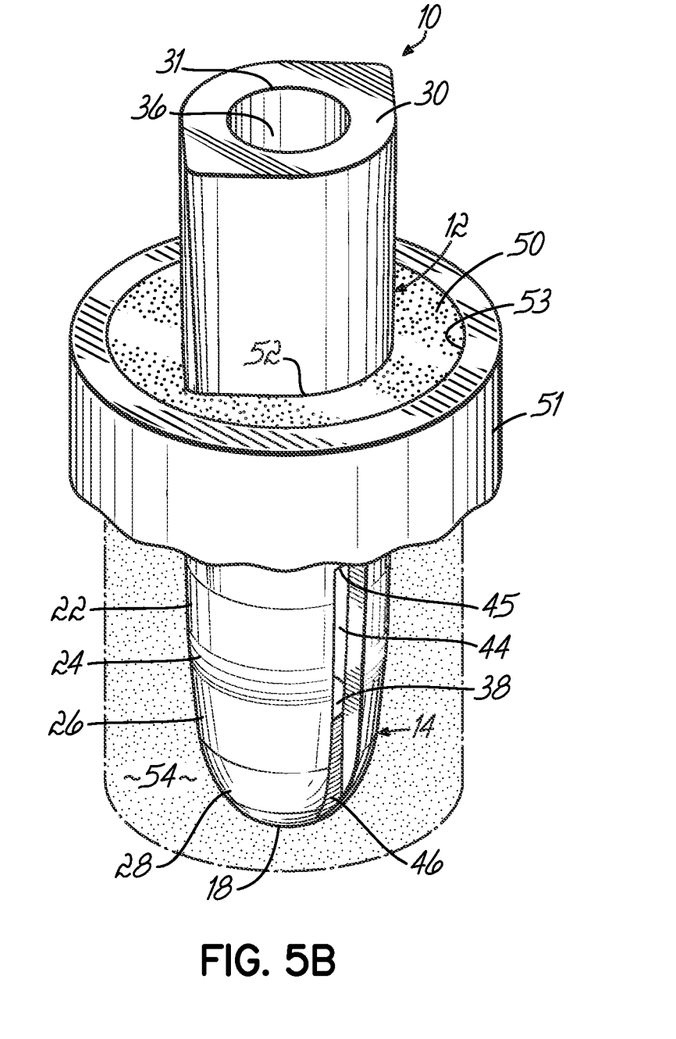

With reference to FIG. 5A, there is shown a perspective view of the blunt cannula 10 and a septum 50 held by a rigid structure 51 and having a slit 52. Septum 50 is held in position by structure 51 so as to close off an aperture 53 to a fluid path as at 54 below septum 50. Cannula 10 is oriented relative to slit 52 such that the major diameter (D.sub.MAJ) of cannula proximal portion 12 is aligned therewith. In use, blunt cannula is inserted into slit 52 with tip end 18 impacting against septum 50 thereat to begin to open slit 52. The distal portion 14 enters into slit 52 with what is believed to be acceptably low insertion forces until proximal portion 12 resides within slit 52 and fluid opening(s) 44 are in the fluid path 54 as seen in FIG. 5B. It is believed that slit 52 does not normally open into a circular shape but instead more of a shape compatible with an oval such that with proximal portion 12 aligned and extending therein as seen in FIG. 5B, an effective seal is achieved with blunt cannula 10 thereat. End 30 may be coupled to or integrally formed with other structure for fluidic communication with lumen 36 via opening 31, such as a male or female luer lock, a syringe end, or other medical fluid connections.

The tapering of proximal and distal portions 12 and 14 presents a significant taper along substantially the entire length of cannula 10, but it is believed that with the foregoing arrangement, kickback is not problematic.

Figure 6:
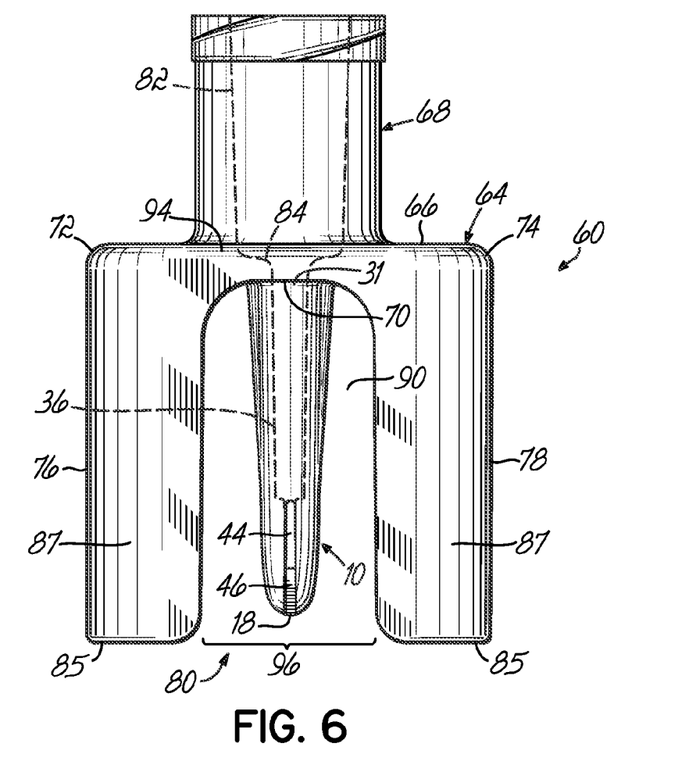
FIG. 6 is a side elevation view of an adaptor including the blunt cannula of FIG. 1 in accordance with the principles of the present invention.
Figure 7:
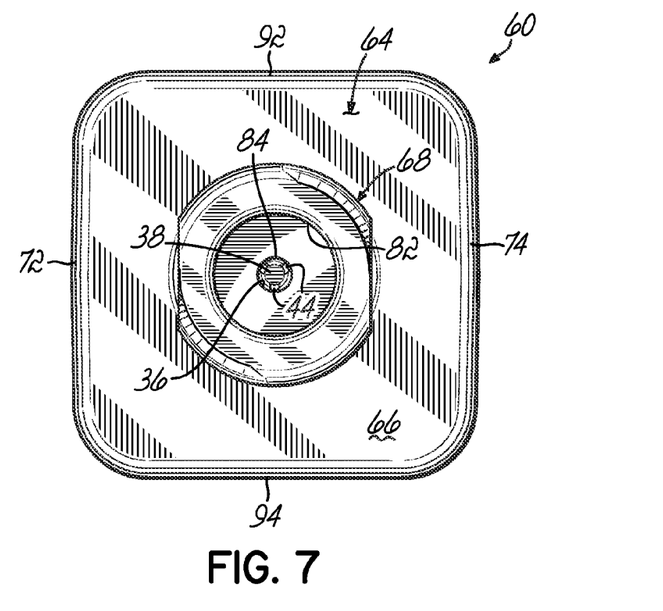
FIG. 7 is a top plan view of the adaptor of FIG. 6.
Figure 8:
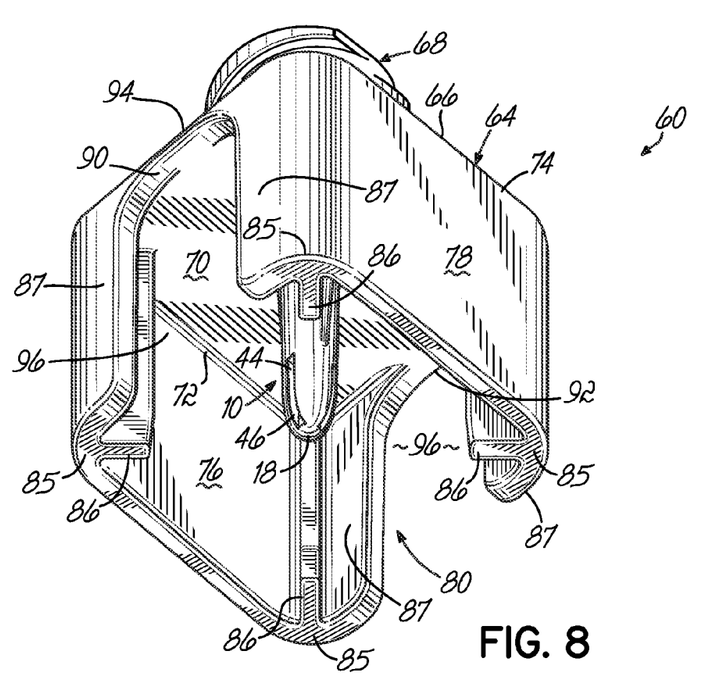
FIG. 8 is bottom perspective view of the adaptor of FIG. 6.
Figure 9:
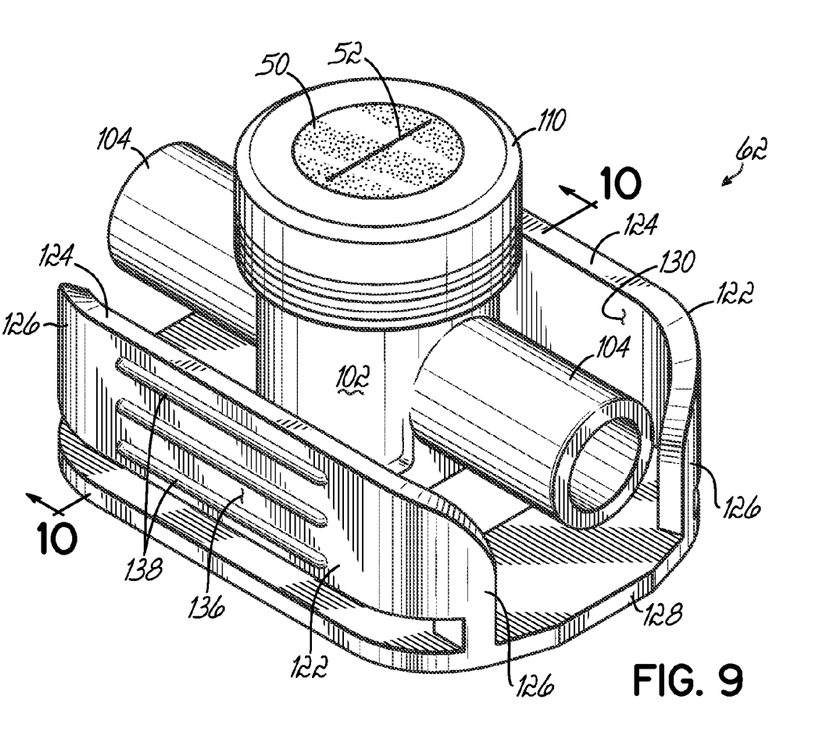
FIG. 9 is a perspective view of one embodiment of a sample site for use with adaptor of FIG. 6 in accordance with the principles of the present invention.

In accordance with yet another aspect of the present invention, the blunt cannula with the non-circular cross-section proximal portion 12 and/or the non-uniform tapered distal portion 14 may form part of an adaptor 60 for accessing a medical site 62 (FIG. 9). To that end, and as shown in FIGS. 6 through 8, adaptor 60 includes a plate 64 having an upper surface 66 with which is associated luer mating structure such as a male luer lock 68, and a lower surface 70 with which a blunt cannula, such as cannula 10, is associated. Plate 64 includes oppositely disposed edges 72, 74 extending between surfaces 66 and 70 and from which extend a pair of generally flat guide walls 76, 78. Walls 76, 78 are to either side of blunt cannula 10 and may extend distally slightly past tip end 18, but may be spaced far enough apart to define a distal mouth 80 that is large enough not to preclude a finger from touching blunt cannula 10, and particularly tip end 18 thereof. Advantageously, walls 76, 68 may be spaced equidistant from cannula 10 such that cannula 10 is in the center of adaptor 60. Central lumen 36 of cannula 10 fluidically couples into the luer cavity 82 of male luer lock 68 as at opening 84 coupled to opening 31 of cannula 10 as best shown in FIG. 6.

Guide walls 76, 78 have lateral edges as at 85, one or more of which may be provided with a rib 86 along a radial of the centerline of cannula 10 so as to be aimed toward cannula 10. Further, lateral edges 85 may extend as at 87 into the area 90 below the intermediate edges 92, 94 of plate 64, but if they do so extend, may advantageously form a gap 96 therebetween.

Figure 10:
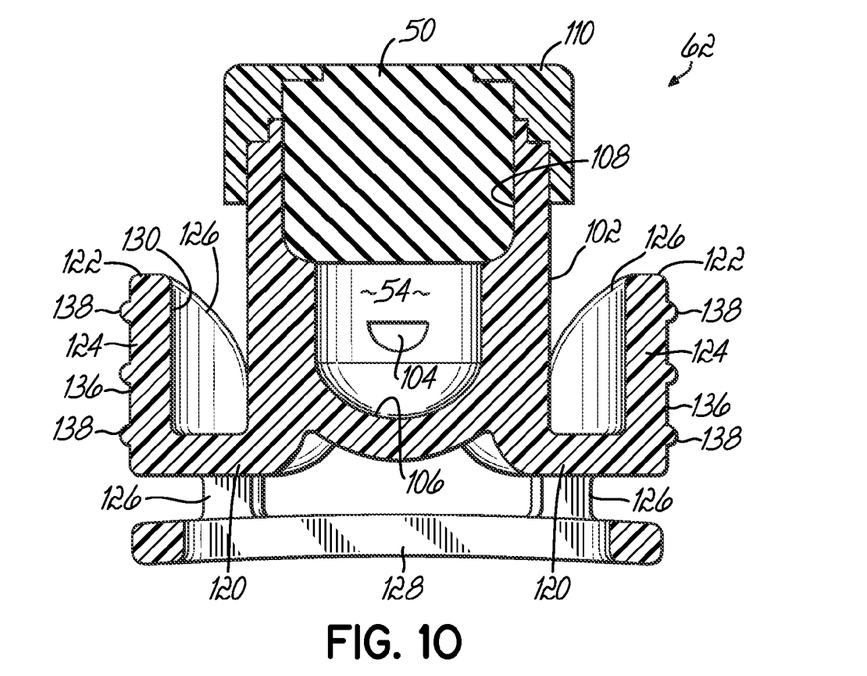
FIG. 10 is a cross-sectional view of the sample site of FIG. 9 taken along line 10-10.
Figure 11:
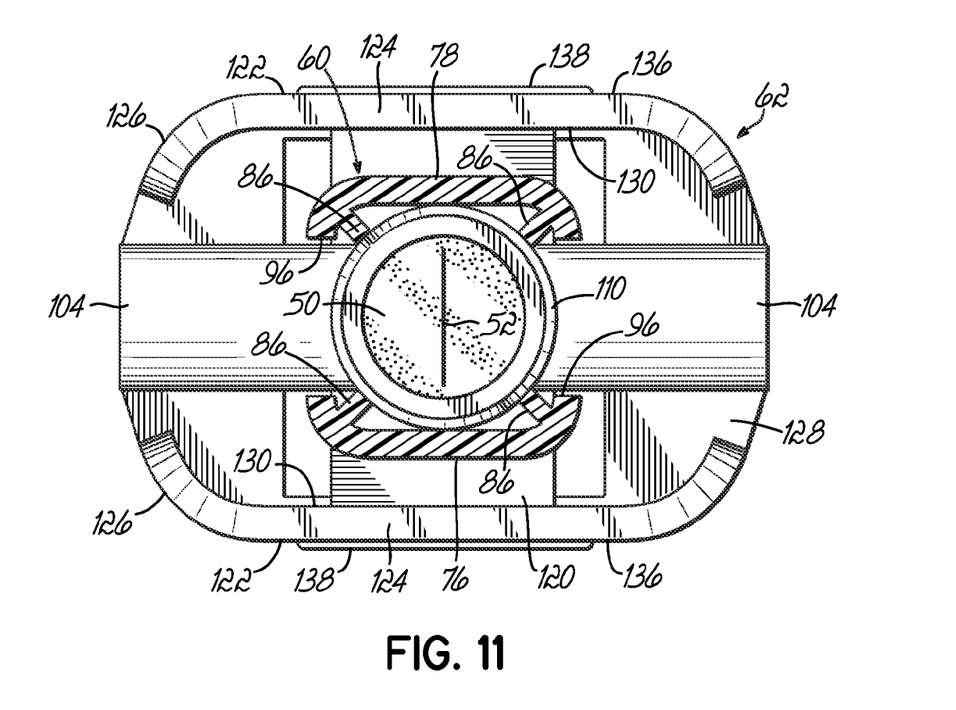
FIG. 11 is a transverse cross-sectional view of the sample site of FIG. 9 with the adapator of FIG. 6 mounted thereon.

The adaptor 60 may be used with a medical site such as a sample site 62 shown in FIGS. 9, 10, and 11. To that end, sample site 62 has a central, cylindrical and circular cross-section housing 102 with oppositely disposed ports 104 extending therefrom to define a T-shape to site 62 (FIG. 9). Fluid normally flows (as at 54) between ports 104 and through cavity 106 within housing 102 and may be as shown in U.S. Pat. No. 5,221,271. Housing 102 includes an aperture 108 adjacent cavity 106 which is closed off by septum 50 with slit 52 thereof in a fixed orientation relative to the path of flow between ports 104, such as tangent or perpendicular thereto as shown in FIG. 9. Septum 50 may be secured in aperture 108 by a cap 110 bonded to housing 102 thereat. Adaptor 60 is sized to cooperate with sample site 62. To that end, guide walls 76, 78 are spaced apart a distance approximating the width or diameter of central housing 102 transverse to the ports 104 (see FIG. 11) so as to fit closely thereover with tip end 18 of cannula 10 aimed at slit 52. Further, cannula 10 may be held in adaptor 60 at a fixed orientation such that the major axis ($D_{MAJ}$) of proximal portion 12 of cannula 10 is aligned with slit 52. To that end, the major axis ($D_{MAJ}$) advantageously extends transversely between guide walls 76 and 78.

The rib(s) 86 also help to align cannula 10 with slit 52. The gap(s) 96 are sized to receive a respective port 104 therethrough so as not to impede insertion of cannula 10 into septum 50, while also advantageously reducing the likelihood of rotation of adaptor 60 relative to housing 102.

Housing 102 may be supported on struts 120 which extend and are coupled to outboard support walls 122, each having an elongated flat portion 124 and lateral arcuate edges 126, the latter being secured to bracket 128. The flat portions 124 each define an inner surface 130 confronting housing 102 and an outer surface 136 facing away from housing 102. One or more ridges 138 are disposed on the outer surface(s) 136 of flat portion(s) 124 to facilitate gripping site 62. Ridges 138 each extend in a line in the same direction as the elongated flat portion on to which they are disposed so as not to form radially inwardly or outwardly curvatures thereof relative to housing 102.

Figure 12:
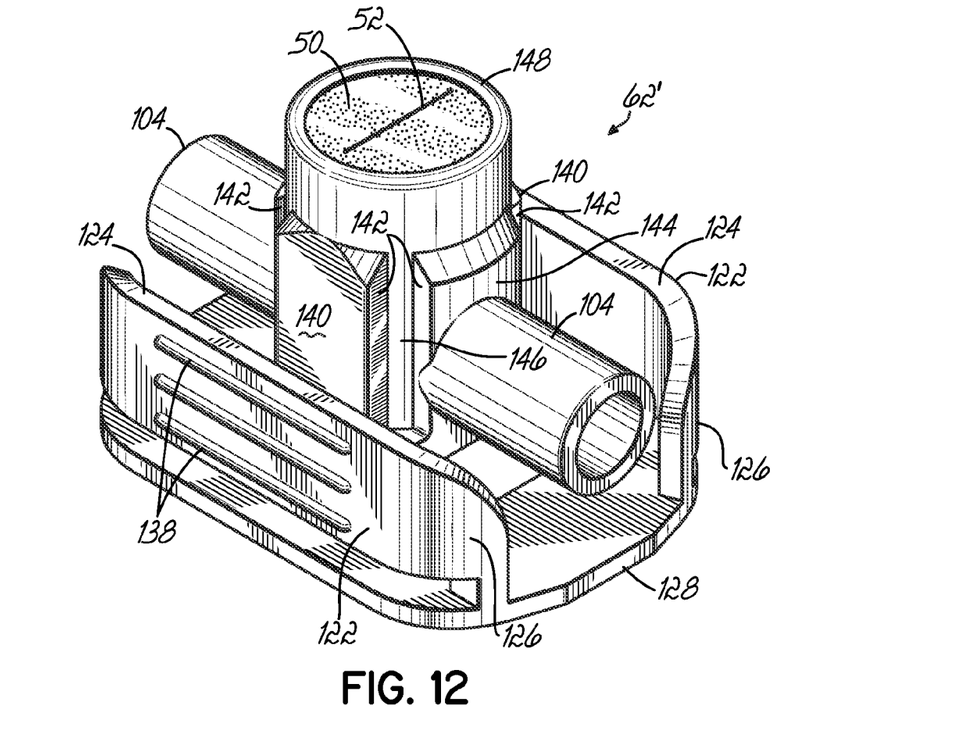
FIG. 12 is a perspective view of another embodiment of a sample site for use with the adaptor of FIG. 1 in accordance with the principles of the present invention.
Figure 13:
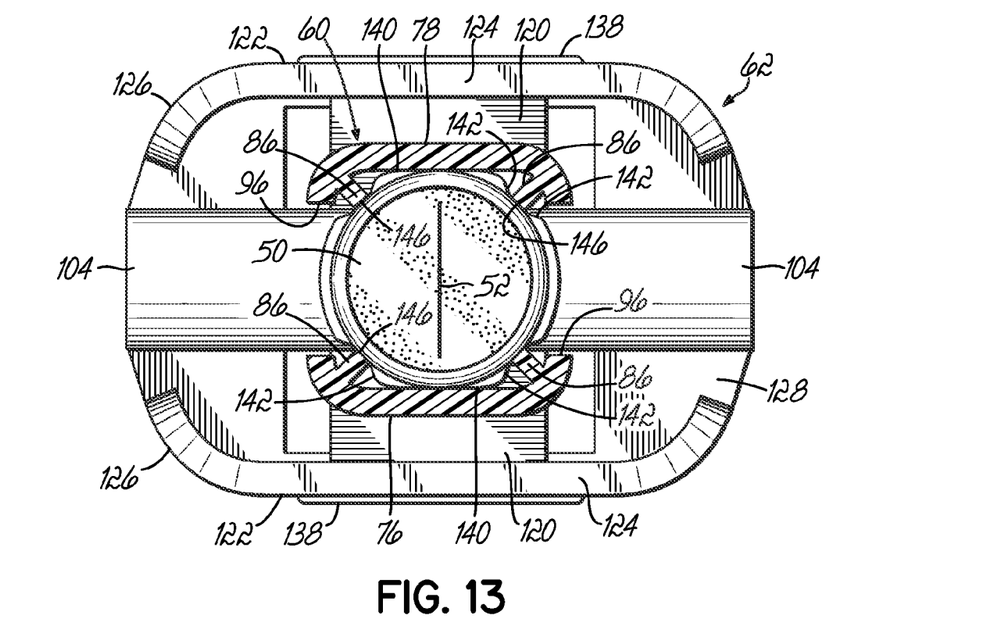
FIG. 13 is a transverse cross-sectional view of the sample site of FIG. 12 with the adaptor of FIG. 6 mounted thereon.

An alternative sample site 62' is shown in FIGS. 12 and 13 in which at least the outboard aspects of housing 102 between ports 104 are generally flat side walls 140 such as by thickening the plastic of housing 102 thereat. Side walls 140 matingly align with guide walls 76, 78 and further resist rotation therebetween (see FIG. 13). In the embodiment of FIG. 12, one or more of the lateral edges 142 of walls 140 define a groove edge to receive a respective rib 86 therealong to still further enhance alignment and/or resist rotation. Alternatively, or additionally, the adjacent side walls 144 could also be thickened so as to cooperate with walls 140 to define grooves 146 therebetween bounded by groove edges 142 for receiving the rib(s) 86. Also, septum 50 may be held to housing 102 by swaging the upper end of the housing thereover as at 148.

In use, ports 104 of site 62 typically are connected to tubing such as in a closed blood sampling system. The cavity 106 of site 62 may be accessed by blunt cannula 10 to withdraw fluid from cavity 106. To that end, a syringe (not shown) may be coupled to luer connector 68 and adaptor 60 is positioned with guide walls 76, 78 to either side of housing 102 and ports 104 aligned with gaps 96. The user (not shown) may grip site 62 by support walls 122 and push adaptor 60 down over housing 102 to insert cannula 10, tip end 18 first, into slit 52 with the major diameter ($D_{MAJ}$) of proximal portion 12 aligned with slit 52. The adaptor 60 may be pushed into place until the guide walls 76, 78 hits against struts 120 whereat portion 12 extends into slit 52 and distal portion 14 is in the cavity 106 so as to communicate with fluid path 54 extending therein as seen in FIG. 11 (or FIG. 13 when used with site 62'). Septum 50 seals to cannula 10 for withdrawal of fluid into lumen 36 (or expulsion of fluid from lumen 36 were adaptor 60 or blunt cannula 10 coupled to an injection site such as a heparin lock (not shown)). The resiliency of the elastomeric material of septum 50 about cannula 10 holds adaptor 60 in place without the need for locking structure, although such could be added or included if desired. After use, adaptor 60 is pulled off from site 62 whereupon slit 52 closes to maintain the closure of aperture 108.

While the present invention has been illustrated by the description of embodiments thereof, and while the embodiments have been described in considerable detail, it is not intended to restrict or in any way limit the scope of the appended claims to such detail. Additional advantages and modifications will readily appear to those skilled in the art. The invention in its broader aspects is, therefore, not limited to the specific details, representative apparatus and method, and illustrative examples shown and described. Accordingly, departures may be made from such details without departing from the spirit or scope of the general inventive concept.

Having described the invention, what is claimed is:

1. A blunt cannula comprising:
an elongated, rigid tubular member sized to be received into a slit septum, the rigid tubular member having a proximal portion extending distally from a proximal end and a distal portion extending distally from the proximal portion and terminating in a rounded tip end, the proximal portion having a non-circular cross-section, the distal portion including a plurality of tapered segments having different tapers, any first cross-section of the rigid tubular member taken distally of the proximal end being no larger than a second cross-section taken of the rigid tubular member distally of the proximal end and proximal of the first cross-section, wherein the proximal and distal portions of the rigid tubular member are tapered such that the rigid tubular member is tapered with a non-zero taper along substantially an entire length thereof;
a central lumen extending through the proximal portion and into the distal portion;
at least one fluid opening communicating through an aspect of the distal portion with the central lumen; and
at least one groove coupled to the at least one fluid opening so as to be in fluid communication therewith and extending along the distal portion from the at least one fluid opening to the tip end.

2. The blunt cannula of claim 1, the proximal portion having a generally oval cross-section.

3. The blunt cannula of claim 2, the proximal portion of the blunt cannula tapering toward the distal portion such that a major diameter of the generally oval cross-section decreases toward the distal portion.

4. The blunt cannula of claim 3, the distal portion being tapered between the proximal portion and the tip end.

5. The blunt cannula of claim 1, the proximal portion of the blunt cannula tapering toward the distal portion.

6. The blunt cannula of claim 5, the distal portion being tapered between the proximal portion and the tip end.

7. The blunt cannula of claim 1 in combination with a medical site including a slit septum for receiving the blunt cannula therethrough.

8. The combination of claim 7, the medical site being a sample site.

9. The blunt cannula of claim 1, the distal portion being tapered between the proximal portion and the tip end.

10. The blunt cannula of claim 1, wherein the non-circular cross section of the proximal portion is oval-shaped such that a major diameter of the oval shape is configured to be aligned with an opening slit of the septum.

11. The blunt cannula of claim 1, wherein the non-circular cross section of the proximal portion is oval-shaped such that a major diameter of the oval shape is configured to be aligned with an opening slit of the slit septum.

12. A blunt cannula comprising:
an elongated, rigid tubular member sized to be received into a slit septum, the rigid tubular member having a proximal portion extending distally from a proximal end and a distal portion extending distally from the proximal portion and terminating in a rounded tip end, the distal portion including a plurality of tapered segments located proximally of the rounded tip end and having different tapers, each of the plurality of tapered segments including a proximal end and a distal end and defining a non-zero taper along an entire length between the proximal and distal ends of each of the plurality of tapered segments, the respective proximal end and distal end of any pair of adjacent tapered segments in the plurality of tapered segments touching each other, any first cross-section of the rigid tubular member taken distally of the proximal end being no larger than a second cross-section taken of the rigid tubular member distally of the proximal end and proximal of the first cross-section, wherein the proximal and distal portions of the rigid tubular member are tapered such that the rigid tubular member is tapered along substantially an entire length thereof;

a central lumen extending through the proximal portion and into the distal portion; and at least one fluid opening extending into the distal portion and along at least two of the plurality of tapered segments, the at least one fluid opening communicating through an aspect of the distal portion with the central lumen.

13. The blunt cannula of claim 12 having four tapered segments, including a first tapered segment adjacent the proximal portion, a second tapered segment adjacent the first tapered segment, a third tapered segment adjacent the second tapered segment, and a fourth tapered segment adjacent the third tapered segment and closer to the tip end than the other three tapered segments.

14. The blunt cannula of claim 13, the lumen extending into the distal portion through at least the first and second tapered segments.

15. The blunt cannula of claim 13, the first and third tapered segments being conically tapered, with a conical taper of the third segment being greater than a conical taper of the first tapered segment.

16. The blunt cannula of claim 15, the second and fourth tapered segments being arcuately tapered each with a respective radius of curvature, a radius of curvature of an arcuate taper of the fourth tapered segment being less than a radius of curvature of an arcuate taper of the second tapered segment.

17. The blunt cannula of claim 13, at least an aspect of the fourth tapered segment being solid, the lumen extending into the distal portion short of the solid aspect.

18. The blunt cannula of claim 13, the fourth tapered segment and at least an aspect of the third tapered segment adjacent the fourth tapered segment being solid, the lumen extending into the distal portion short of the solid aspect of the third segment.

19. The blunt cannula of claim 13, the second and fourth tapered segments being arcuately tapered each with a respective radius of curvature, a radius of curvature of an arcuate taper of the fourth tapered segment being less than a radius of curvature of an arcuate taper of the second tapered segment.

20. The blunt cannula of claim 12 wherein the proximal portion has a non-circular cross-section.

21. The blunt cannula of claim 20 wherein the proximal portion has a generally oval cross-section.

22. The blunt cannula of claim 21, the proximal portion being tapered such that a major diameter of the generally oval cross-section decreases toward the distal portion.

23. The blunt cannula of claim 12, the tip end being solid.

24. The blunt cannula of claim 23, the lumen extending into the distal portion short of the tip end.

25. The blunt cannula of claim 12, a one of the plurality of tapered segments being closer to the tip end than at least another of the plurality of tapered segments, an aspect of the one tapered segment being solid, the lumen extending into the distal portion short of the solid aspect.

26. The blunt cannula of claim 25, the one of the plurality of tapered segments being closer to the tip end than any other of the plurality of tapered segments, the one of the plurality of tapered segments being completely solid, the lumen extending into the distal portion short of the one of the plurality of tapered segments.

27. The blunt cannula of claim 12 further comprising at least one groove extending along the distal portion between the at least one fluid opening and the tip end.

28. The blunt cannula of claim 27, the tip end being solid, the at least one groove stopping short of the tip end.

29. The blunt cannula of claim 12 in combination with a medical site including a slit septum for receiving the blunt cannula therethrough.

30. The combination of claim 29, the medical site being a sample site.

31. The blunt cannula of claim 12, at least one of the plurality of tapered segments having a conical taper and at least another of the plurality of tapered segments having an arcuate taper.

32. The blunt cannula of claim 12 further comprising a plate having an upper surface and a lower surface and oppositely disposed side edges therebetween, luer mating structure associated with the plate upper surface, the proximal portion of the blunt cannula associated with the lower surface; and a pair of guide walls extending from the oppositely disposed side edges to either side of the blunt cannula.

33. A blunt cannula comprising:

an elongated, rigid tubular member sized to be received into a slit septum, the rigid tubular member having a proximal portion extending distally from a proximal end and a distal portion extending distally from the proximal portion and terminating in a solid, rounded tip end, the distal portion having a non-uniform taper defined by four tapered segments located proximally of the rounded tip end, the four tapered segments including a first tapered segment adjacent the proximal portion, a second tapered segment adjacent the first tapered segment, a third tapered segment adjacent the second tapered segment, and a fourth tapered segment adjacent the third tapered segment and closer to the tip end than the other three tapered segments, each tapered segment having a different taper from the other tapered segments, each of the four tapered segments including a proximal end and a distal end and defining a non-zero taper along an entire length between the proximal and distal ends of each of the four tapered segments, the respective proximal end and distal end of any pair of adjacent tapered segments of the four tapered segments touching each other, the fourth tapered segment being solid, any first cross-section of the rigid tubular member taken distally of the proximal end being no larger than a second cross-section taken of the rigid tubular member distally of the proximal end and proximal of the first cross-section, wherein the proximal and distal portions of the rigid tubular member are tapered such that the rigid tubular member is tapered along substantially an entire length thereof;

a central lumen extending through the proximal portion and into the distal portion through at least the first and second tapered segments, but not into the fourth tapered segment and the solid tip end; and at least one fluid opening extending into the distal portion along at least two of the four tapered segments and coincident with the central lumen therein, the at least one fluid opening not extending into the distal portion coincident with the fourth tapered segment or the tip end.

34. The blunt cannula of claim 33 further comprising a plurality of circumferentially spaced fluid openings extending into the distal portion coincident with the central lumen therein and not into the distal portion coincident with the fourth tapered segment and the tip end.

35. The blunt cannula of claim 34 further comprising a plurality of circumferentially spaced grooves extending along the distal portion of the cannula from a respective fluid opening toward the tip end.

36. The blunt cannula of claim 35, the plurality of circumferentially spaced grooves stopping short of the tip end.

37. The blunt cannula of claim 33 further comprising a groove extending along the distal portion of the cannula from the at least one fluid opening toward the tip end.

38. The blunt cannula of claim 37, the groove stopping short of the tip end.

39. The blunt cannula of claim 33 in combination with a medical site including a slit septum for receiving the blunt cannula therethrough.

40. The combination of claim 39, the medical site being a sample site.

41. The blunt cannula of claim 33 further comprising a plate having an upper surface and a lower surface and oppositely disposed side edges therebetween, luer mating structure associated with the plate upper surface, the proximal portion of the blunt cannula associated with the lower surface; and a pair of guide walls extending from the oppositely disposed side edges to either side of the blunt cannula.

42. A blunt cannula comprising:
an elongated, rigid tubular member sized to be received into a slit septum, the rigid tubular member having a proximal portion extending distally from a proximal end and a distal portion extending distally from the proximal portion and terminating in a solid, rounded tip end, the proximal portion having a non-circular cross-section, the distal portion having a non-uniform taper defined by four tapered segments, the four tapered segments including a first tapered segment adjacent the proximal portion, a second tapered segment adjacent the first tapered segment, a third tapered segment adjacent the second tapered segment, and a fourth tapered segment adjacent the third tapered segment and closer to the tip end than the other three tapered segments, each tapered segment having a different taper from the other tapered segments, the fourth tapered segment being solid, any first cross-section of the rigid tubular member taken distally of the proximal end being no larger than a second cross-section taken of the rigid tubular member distally of the proximal end and proximal of the first cross-section, wherein the proximal and distal portions of the rigid tubular member are tapered such that the rigid tubular member is tapered along substantially an entire length thereof;
a central lumen extending through the proximal portion and into the distal portion through at least the first and second tapered segments, but not into the fourth tapered segment and the solid tip end;
at least one fluid opening extending into the distal portion coincident with the central lumen therein, the at least one fluid opening not extending into the distal portion coincident with the fourth tapered segment or the tip end; and
at least one groove coupled to the at least one fluid opening so as to be in fluid communication therewith and extending along the distal portion from the at least one fluid opening to the tip end.

43. The blunt cannula of claim 42, wherein the non-circular cross section of the proximal portion is oval-shaped such that a major diameter of the oval shape is configured to be aligned with an opening slit of the slit septum.

* * * * *